United States Patent [19]

Lee et al.

[11] Patent Number: 5,387,695
[45] Date of Patent: Feb. 7, 1995

[54] PROCESS FOR THE CHEMICAL RESOLUTION OF 5-ALKOXY-SUBSTITUTED (+)-1,3-DIMETHYLOXINDOLYLETHYLAMINES

[75] Inventors: Thomas B. K. Lee, Whitehouse Station; George S. K. Wong, Fort Lee, both of N.J.

[73] Assignee: Hoechst-Roussel Pharmaceuticals, Inc., Somerville, N.J.

[21] Appl. No.: 22,605

[22] Filed: Feb. 17, 1993

Related U.S. Application Data

[63] Continuation of Ser. No. 831,750, Feb. 10, 1992, abandoned, which is a continuation of Ser. No. 640,505, Jan. 3, 1991, abandoned, which is a continuation of Ser. No. 409,213, Sep. 19, 1989, abandoned.

[51] Int. Cl.⁶ ............................................. C07D 209/34
[52] U.S. Cl. ...................................... 548/486; 548/495
[58] Field of Search ................................ 548/486, 495

[56] References Cited

U.S. PATENT DOCUMENTS 4,072,698  2/1978  Hylton et al.
5,274,117  12/1993 Lee .......................................... 548/486

OTHER PUBLICATIONS

Howe et al CA 83:57233w (1975).
Kamiteri et al CA 85:108849c (1976).
Remy et al Ca 87:193907d (1977).
Yost et al CA 92:94098u (1980).
Zoeless et al CA 104:206931d (1986).
Mahata et al CA 107:58592u (1987).

Mahato et al., "A new synthetic route to aromatic glyoxals." CA 107:58591n (1987).
Zoelss et al., "S(-)-Celiprolol, its pharmaceuticlally acceptable salts, and pharmaceutical compositions," CA 104:206931d (1986).
Yost et al., "Resolution of (±)-propranolol." CA 92:94098n (1980).
Remy et al., "(+)-and (−)(-)3-Methoxycyproheptadine. A comparative evaluation of the antiserotonin, antihistaminic, anticholinergic, and orexigenic properties with cyproheptadine." CA 87:193907d (1977).
Kametani et al., "The optical resolution of (±)-galanthamine." CA 85:108849c (1976).
Howe et al., "Optically active morpholine derivatives." CA 83:57233w (1975).

*Primary Examiner*—Celia Chang
*Attorney, Agent, or Firm*—Finnegan, Henderson, Farabow, Garrett & Dunner

[57] ABSTRACT

A process for chemically resolving a mixture of enantiomers of primary amines, such as enantiomers of 1,3-dimethyl-5-methoxyoxindolylethylamine, provides one of the enantiomers in the form of a tartaric acid salt. In carrying out the process, an enantiomeric mixture is contacted with a chiral acid in an amount sufficient to preferentially precipitate a salt of the chiral acid and one of the enantiomers. The resulting precipitate can then be recovered. The chiral acid is selected from the group consisting of dibenzoyl-D-tartaric acid, dibenzoyl-L-tartaric acid, ditoluoyl-D-tartaric acid, and ditoluoyl-L-tartaric acid. The precipitates can be used in the synthesis of stereospecific forms of physostigmine.

25 Claims, No Drawings

PROCESS FOR THE CHEMICAL RESOLUTION OF 5-ALKOXY-SUBSTITUTED (+)-1,3-DIMETHYLOXINDOLYLETHYLAMINES

This application is a continuation application of Ser. No. 07/831,750, filed Feb. 10, 1992, now abandoned, which is continuation of Ser. No. 07/640,505, filed Jan. 3, 1991, now abandoned, which is a continuation of Ser. No. 07/409,213, filed Sep. 19, 1989, now abandoned.

BACKGROUND OF THE INVENTION

This invention relates to a process for the chemical separation of stereoisomers. More particularly, this invention relates to a process of using a chiral acid for resolving mixtures of enantiomers of primary amines that are useful in the synthesis of (+)-physostigmine and (−)-physostigmine.

The cholinergic neuronal system can be found in the central nervous system (CNS), in the autonomic nervous system, and in the skeletal motor system. Acetylcholine (ACh) is the neurotransmitter in all ganglia, the neuromuscular junction, and the post-ganglionic synapses of the cholinergic nervous system. Acetylcholine is normally an excitatory neurotransmitter that binds to nicotinic and muscarinic receptors.

Acetylcholinesterase (ACHE) is an enzyme that hydrolyres and thereby deactivates ACh after it binds to a receptor. This enzyme is present in all peripheral and central junctional sites and in certain cells of the body.

In some circumstances, it is desirable to stimulate acetylcholine receptors. One method involves the use of indirect agonists, such as anticholinesterase drugs, which inhibit the hydrolysis of ACh by ACHE. When an anticholinesterase drug blocks AChE and inhibits the destruction of released ACh, a higher neurotransmitter level and increased biological response result. The alkaloid, physostigmine, which can be isolated from the seeds of the Calabar bean, has been found to be particularly effective as an anticholinesterase drug. Physostigmine has a high affinity for AChE and is capable of inhibiting AChE for prolonged periods.

It is believed that degeneration of the cholinergic pathways in the CNS and the resultant development of apparent irregularities in neuron arrangement may be a principal cause of senile dementia of the Alzheimer type. This disease leads to progressive regression of memory and learned functions. Since the average age of the population is on the increase, the frequency of Alzheimer's disease is increasing and requires urgent attention.

It has been suggested that cholinergic agonists, such as the anticholinesterase drugs, are useful in the treatment of Alzheimer's disease. Nevertheless, drug treatment with anticholinesterase drugs has not proved entirely satisfactory. Thus, there is a need in the art for new forms of drugs for the treatment of this disease.

The enantiomers of physostigmine are under investigation for the treatment of Alzheimer's disease. In order to satisfy the need for physostigmine enantiomers having the highest pharmaceutical activity, there exists a need in the art for a process for preparing the enantiomers. Specifically, the enantiomer (−)physostigmine is of current interest, and while methods for preparing physostigmine have been proposed, there exists a need in the art for a stereoselective process for producing the S- or (−)-form.

It has been found that the compound 1,3-dimethyl-5-methoxyoxindolylethylamine is an important intermediate in a recently discovered method of synthesizing (−)-physostigmine. While this amine can be prepared using conventional techniques, a racemic mixture is usually formed. Resolution of the racemic amine mixture into its R and S components would make it possible to synthesize (+)-physostigmine and (−)-physostigmine.

Resolution of mixtures of enantiomers, however, is very much a matter of trial and error. Even experienced investigators find that certain compounds resist chemical resolution by any one of a number of combinations of resolving agents and reaction conditions. As a general rule, investigators in the art of separating stereoisomers commence a study by using reagents and conditions that have been found to be successful in the past in resolving similar compounds.

A racemic mixture of the compound 1,3-dimethyl-5-ethoxyindolylethylmethylamine is known in the art. The racemic mixture has been resolved by the successive actions of d-camphor-sulphonic acid and d-tartaric acid. Julian et al., J. Chem. Soc., (1935), 755–757. Even though this compound bears a structural resemblance to the compound 1,3-dimethyl-5-methoxyindolylethylamine, which is the intermediate used in the synthesis of (±)-physostigmine, application of the same strategy to a racemic mixture of the latter compound has not been successful, thus confirming the unpredictability of chemical resolution techniques.

Thus, in addition to the need for stereoselective methods for producing enantiomers of physostigmine, there also exists a need in the art for methods for preparing intermediates for use in the stereoselective process. The method should make it possible to obtain the intermediates in a state of high optical purity. In addition, the process should be easy to carry out and should employ reagents that are readily available.

SUMMARY OF THE INVENTION

Accordingly, this invention aids in fulfilling these needs in the art by providing a process for treating an enantiomeric mixture of primary amines, such as 1,3-dimethyl-5-methoxyoxindolylethylamine, with a chiral acid to precipitate one of the enantiomers from the mixture. The process of the invention comprises providing a solution consisting essentially of a mixture of enantiomers of the following formulas:

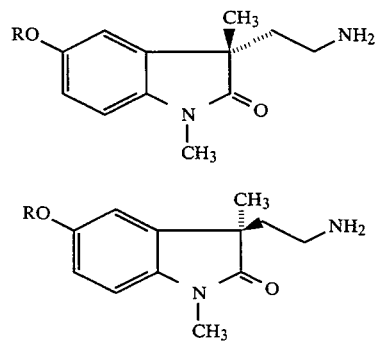

where R is a straight chain or branched alkyl group having 1-3 carbon atoms or benzyl.

The mixture of enantiomers is contacted with a chiral acid selected from the group consisting of dibenzoyl-D- tartaric acid, dibenzoyl-L-tartaric acid, ditoluoyl-D-tartaric acid, and ditoluoyl-L-tartaric acid, in an amount sufficient to preferentially precipitate a salt of the chiral acid and one of the enantiomers.

The precipitates that are formed in the process of this invention can be used in the synthesis of stereospecific forms of physostigmine and physostigmine-like compounds. In particular, the S-form of 1,3-dimethyl-5-methoxyoxindolylethylamine, which is referred to herein as amine 1a, is obtained as a precipitate which is useful for preparing (−)-physostigmine. The R-form of this compound is referred to as amine 1b.

DETAILED DESCRIPTION OF PREFERRED EMBODIMENTS

The process of this invention is useful for resolving enantiomeric mixtures of 1,3-dimethyl-5-alkoxyoxindolylethylamines, such as 1,3-dimethyl-5-methoxyoxindolylethylamine. While the primary amine 1,3-dimethyl-5-methoxyoxindolylethylamine will be frequently mentioned hereinafter, it will be understood that the following detailed description equally applies to the other primary amine enantiomers employed in the process of this invention.

The enantiomers in the enantiomeric mixture are resolved by converting both of the enantiomers to a pair of diastereomeric salts. Different solubility characteristics make it possible to preferentially isolate one of the salts. More particularly, a reaction mixture containing both of the enantiomers in solution is allowed to interact with an optically active derivative of tartaric acid to form a salt. The salt readily forms a precipitate in the reaction mixture. The enantiomer in an optically purified state can be recovered from the precipitate by treatment with a mineral base.

The following nomenclature and conventions are employed in the detailed description of this invention. As used herein, the terms "resolve" and "resolution" are intended to encompass the complete or partial separation of the two enantiomers of the 5-alkoxy-substituted 1,3-dimethylindolylethylamines. Thus, the terms are intended to cover separations in which only one of the enantiomers is obtained in a pure state. In addition, the terms are intended to encompass some degree of separation of the enantiomers, but in which neither of the enantiomers is obtained completely free of the other. Separation of the enantiomers according to the process of this invention may or may not be quantitative.

The process of this invention is useful for separating the enantiomers from solutions of the enantiomers in organic solvents. The solution can contain an equal or nearly equal number of molecules of each of the enantiomers, in which case, the solution will be a racemic mixture or a racemic modification. The invention can also be employed with solutions in which one of the enantiomers predominates due to an unequal number of molecules of each enantiomer in solution.

As used herein, the expressions "enantiomeric mixture" and "mixture of enantiomers" are used interchangeably to refer to racemic modifications of the enantiomers. The expressions also include solutions containing both of the enantiomers, wherein the solutions exhibit either (+) or (−) optical rotation as observed and measured with a polarimeter.

The heavy line in the form of a wedge▶ in the formulas herein signify that the substituents are above the average plane of the ring system in connection with which the wedge appears. The heavy broken lines in the form of a wedge▶▶ signify that the substituents are below the average plane of the ring system. In the formula for the primary amine, the methyl group in the 3-position is above the average plane of the indole ring, whereas the aminoethyl group is below the average plane of the ring. Thus, the methyl group and the aminoethyl group are trans to each other relative to the average plane of the ring.

As previously described, the preferred enantiomer of physostigmine is the S or (−)-form because this compound exhibits enhanced activity as an anticholinesterase drug. The compound (−)-physostigmine can be prepared from the S-enantiomer of 1,3-dimethyl-5-methoxyoxindolylethylamine. More particularly, treatment of amine with methyl chloroformate gives the corresponding carbamate, which can be reductively cyclized to esermethole using lithium aluminum hydride. Q. Yu and A. Brossi, Heterocycles, 27:1709–1712 (1988). Demethylation using boron tribromide provides eseroline, which upon reaction with methyl isocyanate provides (−)-physostigmine. Takano, et al., Tetrahedron Letters, 2641–2643 (1982).

The primary amine 1a is an important intermediate in the preparation of (−)-physostigmine. The primary amine should be available in as pure a form of the optical isomer as possible in order to obtain high yields of the (−)- form of physostigmine.

Racemic mixtures of primary amines can be prepared using conventional techniques. For example, an oxindole of the formula:

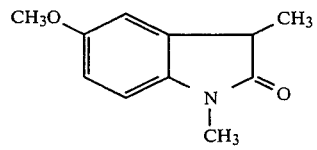

can be prepared by alkylating the —NH₂ group of p-anisidine to form the corresponding —NH—CH₃ group. Utilizing this compound and the synthetic scheme disclosed in Julian et al., J. Chem. Soc., 1935:563–566 and 755–757, the oxindole can be synthesized. The procedure for preparing the oxindole is also described in U.S. Pat. No. 4,791,107.

The oxindole can be converted to an enantiomeric mixture using an achiral phase transfer catalyst. A preferred catalyst for the conversion of oxindole to the mixture of enantiomers is tricaproylmethyl ammonium chloride, which is commercially available under the tradename ALIQUAT 336 from Henkel Corporation or Aldrich Chemical Company. Other achiral phase transfer catalysts, such as tributyl ammonium hydrogen sulfate, can also be employed.

The source of the mixture of enantiomers employed in practicing this invention is generally not critical to the successful operation of the invention. Thus, notwithstanding the foregoing description, it will be understood that the mixture of enantiomers can be formed by any of a variety of known techniques. For example, the mixture can be obtained by mixing the enantiomers in equal or unequal amounts, or by synthesis of dissymmetric molecules starting from either symmetric molecules or a racemic modification, with or without optically active agents or catalysts or symmetric physical influences. The process of this invention for resolving the enantiomers will now be described in greater detail.

It has been found that an enantiomeric mixture of the primary amines can be resolved using a chiral acid. This result was surprising because it was not possible to selectively resolve the enantiomers of the primary amine 1a and 1b using the conventional reagents d-camphor-sulphonic acid and d-tartaric acid.

More particularly, the process of the invention for resolving a mixture of enantiomers is carried out with a chiral acid selected from the group consisting of dibenzoyl-D-tartaric acid, dibenzoyl-L-tartaric acid, ditoluoyl D-tartaric acid, or ditoluoyl-L-tartaric acid. These acids are commercially available, or, in the alternative, they can be prepared using conventional techniques.

The preferred chiral acid for use in the process of this invention is dibenzoyl-D-tartaric acid, because the S-enantiomer of 1,3-dimethyl-5-methoxyoxindolylethylamine can be selectively precipitated from an enantiomeric mixture with this acid in relatively high optical purity. This reagent can be easily prepared or can be commercially obtained at relatively low cost. Furthermore, this acid can be readily and nearly quantitatively recovered after completion of the resolution.

In principle, the enantiomers to be resolved cannot be obtained in a higher state of optical purity than the optical purity of the resolving agent by mere crystallization or precipitation of the diastereomers. Thus, it is preferred that the chiral acid employed as the resolving agent in the process of the invention be in a substantially optically pure state. Nevertheless, the use of an optically pure acid is not required when it is not necessary to achieve complete resolution. In the event of partial resolution, the enantiomer can be further purified by recrystallization as described below.

The nature of the enantiomer that is formed will depend upon the configuration of the chiral acid that is utilized, the amount of the acid, and the concentration of the enantiomers in the solvent. These and other factors relating to the process of the invention will now be described in greater detail.

It has been found that use of the D-form of the chiral acid can be employed to preferentially precipitate enantiomer 1a, while the L-form of the chiral acid can be employed to preferentially precipitate the enantiomer 1b. Thus, this invention makes it possible to enrich the enantiomeric mixture in either one of the two enantiomers and to separate one of the enantiomers from the mixture by proper selection of the chiral acid used as the resolving agent.

The amount of the chiral acid employed in the enrichment process of this invention will generally be about 0.5 to about 1 equivalent of acid per equivalent of the primary amine, and preferably about 0.6 to about 0.7 equivalent. It has been found that the amount of the chiral acid used as the resolving agent can affect the identity of the enantiomer of the primary amine that is preferentially precipitated. For example, when the racemic amine 1a and 1b is treated with one or more equivalents of dibenzoyl-D tartaric acid in an appropriate solvent, such as acetonitrile, the diastereomeric salt corresponding to the R-enantiomer 1b is preferentially precipitated. On the other hand, when less than 1 equivalent of dibenzoyl-D-tartaric acid is employed, the diastereomeric salt corresponding to the S-enantiomer 1a is preferentially precipitated. In the preferred method of carrying out the enrichment process of the invention, the enantiomer 1a is preferentially precipitated from a racemic mixture of 1a and 1b with dibenzoyl-D-tartaric acid in an amount of about 0.6 to about 0.7 equivalent of the acid per equivalent of the primary amine.

The process of the invention is carried out in a solution comprising the enantiomers and the chiral acid. The solution is prepared with an organic solvent in which the enantiomers and the chiral acid are soluble, but in which one of the tartaric acid salts of the enantiomers is insoluble so that one of the salts of the enantiomers will preferentially precipitate.

The solvent is typically a liquid organic compound, such as a cyclic or acyclic substituted hydrocarbon. Ethers, such as diethyl ether, dioxane, and tetrahydrofuran, can be employed. Examples of suitable halogenated solvents are methylene chloride and chloroform. The organic compound can be an aromatic compound, such as toluene or xylene. Aliphatic nitriles, such as acetonitrile and propionitrile, can also be employed.

The preferred solvents for use in this invention are solvents that provide a medium in which individual, well crystallized salts can be formed. The preferred solvents are also those in which the solubilities of the salts of the enantiomers are well-differentiated. In addition, the preferred solvents are those in which there is substantially no formation of molecular complexes, such as double salts of the enantiomers. The preferred solvent for use in the process of this invention is acetonitrile, because this solvent fulfills these criteria.

The ratio of the solvent volume to the amount of enantiomers in the mixture being resolved can be varied over a relatively broad range. The ratio of the amount of solvent to the amount of enantiomers can typically be about 5:1 to about 15:1, where the ratio is expressed as the volume of solvent relative to the weight of the enantiomers in the solvent. Preferably the ratio is about 8:1 to about 12:1. In a preferred process of carrying out this invention, the ratio of the volume of solvent to the weight of enantiomers is about 10:1.

The solution containing the enantiomers can be prepared by dissolving the enantiomeric mixture in the solvent. Dissolution can typically be carried out at a temperature of about 0° C. to about 60° C., but will generally be carried out at room temperature of about 18° C. to about 22° C. Similarly, the chiral acid can be dissolved in a solvent, which is generally the same solvent as the solvent employed for the enantiomeric mixture.

In determining the amount of organic solvent to be used to dissolve the enantiomers and to dissolve the chiral acid, it should be borne in mind that the combined amounts of the solvents relative to the amount of the enantiomers should be within the solvent to enantiomer ratios described above. In one embodiment of the invention, it has been found that one-half of the solvent volume can be used to dissolve the enantiomers and the other half of the solvent volume can be used to dissolve the resolving agent when the solvent is acetonitrile. The relative amounts of the solvents used to dissolve the reagents has not been found to be critical, and different relative proportions can be employed provided that each of the reagents is substantially completely dissolved in the organic solvent before the solutions of the reagents are combined.

The order in which the solutions are mixed has not been found to be critical. The chiral acid solution can be gradually added to the solution of the enantiomers or the order of addition can be reversed. On a laboratory scale, it is preferred to add the solution of the resolving agent dropwise to the solution of the enantiomers.

After the resolving agent is added to the solution of the enantiomers, the resulting solution is aged under conditions to form a precipitate comprising a salt of the chiral acid and the enantiomer that is selectively precipitated. Aging is typically carried out at a temperature of about 0° C. to about 30° C. The use of temperatures within the lower end of this range will generally facilitate the formation of precipitates and increase the yield because the salts are generally less soluble in the solvent at the lower temperatures. On the other hand, the use of temperatures within the upper end of this range will generally provide higher selectivity; that is, formation of one of the salts of the enantiomers will be favored over the other salt.

The process of the invention can be carried out with or without agitation of the reaction medium. While the extent of agitation has not been found to be critical, mild stirring of the reaction medium while the reagents are being mixed and during the aging step has been found to produce favorable results.

It will be understood that the process of this invention produces a salt of one of the enantiomers as a precipitate in a mother liquor containing an excess of the other enantiomer in solution. In a preferred embodiment of this invention, the salt of the enantiomer that is preferentially precipitated is further purified by recrystallization. For example, this can be carried out by dissolving the precipitate in an excess amount of an organic solvent. Recrystallization solvents include mixtures of acetonitrile and methyl ethyl ketone or aqueous acetonitrile. The salt is dissolved at or near the boiling point of the recrystallizing solvent. After complete dissolution, the solution is allowed to cool to room temperature and then aged further at 0° C. to recrystallize the tartaric acid salt. Following this procedure, it has been possible in a single recrystallization step to concentrate an initial crop containing the salt of amine 1a and the salt of amine 1b in a weight ratio of 83:17 to a recrystallized mixture containing the amine salts in a weight ratio of 98:2.

The mother liquor can be further treated in order to (1) recover additional amounts of the enantiomer that was selectively precipitated, or (2) to preferentially recover the enantiomer that was not previously removed by precipitation. For example, when the S-enantiomer 1a is first precipitated by exposing an equal mixture of 1a and 1b to less than 1 equivalent of dibenzoyl-D-tartaric acid, the mother liquor becomes enriched in the R-enantiomer 1b. If the mother liquor is now treated with additional dibenzoyl-D-tartaric acid, the R-enantiomer is preferentially precipitated. One way to obtain additional amounts of the S-enantiomer 1a is to remove the excess R-enantiomer and repeat the procedure.

Alternatively, the enantiomer that was not initially selectively precipitated can be removed from the mother liquor. For example, the chiral acid that was initially employed can be neutralized by basification of the reaction medium to form a water soluble salt of the acid. The reaction medium can be extracted with water to provide a mother liquor consisting essentially of the enantiomers of the primary amine in the organic solvent. The mother liquor can then be treated with a different chiral acid or with an amount of the original chiral acid that will precipitate the enantiomer that is present in excess in the mother liquor. Thus, for example, the S-enantiomer 1a can be removed from the reaction medium using dibenzoyl-D-tartaric acid in a stoichiometric deficiency. The mother liquor can then be treated with dibenzoyl-L-tartaric acid to preferentially precipitate the R-enantiomer 1b. As another example, the R-enantiomer 1b can be preferentially precipitated, and the mother liquor can then be treated under conditions to selectively precipitate the S-enantiomer 1a. This invention thus provides an enrichment process having wide flexibility in resolving enantiomeric mixtures.

Resolution of the enantiomeric mixture according to this invention provides a precipitate of one of the enantiomers in the form of a salt of tartaric acid. The tartaric acid salt can be converted to the corresponding free base by conventional techniques. For example, the tartaric acid salt can be dissolved in water, and the resulting solution can be treated with an aqueous solution comprising a non-toxic inorganic base in an amount sufficient to provide a substantially neutral mixture. Examples of suitable bases include sodium hydroxide, potassium hydroxide, sodium carbonate, and potassium carbonate. The amine is extracted with an organic solvent from the aqueous solution. An organic solvent, such as methylene chloride, ethyl acetate, diethyl ether or toluene, can be employed for this purpose. The organic phase can be separated from the aqueous phase. Evaporation of the solvent from the organic phase provides the amine in the form of a free base, which can generally be utilized without further purification. Conversion of the tartaric acid salt to the corresponding free base can be carried out at ambient temperatures.

The mixture of enantiomers can be resolved according to the process of this invention to provide the individual enantiomers in a state of relatively high optical purity. The optical purity can be expressed as the excess of the enantiomer in the reaction product as a percentage of the total enantiomers in the original solution. The amount of the enantiomer preferentially precipitated is conveniently expressed as the percent enantiomeric excess, which is abbreviated "% ee". The percent enantiomeric excess can be calculated as follows:

$$\% \; ee = \frac{([A] - [B])}{([A] + [B])} \times 100$$

where
  [A] is the concentration of one of the enantiomers, and
  [B] is the concentration of the other enantiomer.

Percent ee (% ee) is determined for the precipitated product. In a completely resolved material, the enantiomeric excess is equal in weight to the total material so that % ee, and thus optical purity, is 100%. The concentration of each of the enantiomers is, of course, expressed on the same basis, and can be expressed on either a weight or molar basis because the enantiomers have the same molecular weight.

The optical purity expressed as % ee obtained by the process of this invention will typically be at least about 50%. An optical purity of about 50% ee to about 80% ee can be attained without further purification by recrystallization. The level of optical purity can be increased to about 96% ee by a single recrystallization step, and even up to 99% ee with two recrystallization steps. Optimum enrichment levels can be achieved with a minimum of experimentation.

As previously noted, it has been found that the amount of the enantiomer preferentially precipitated in the process of this invention is dependent upon the amount of the resolving agent and the volume of solvent in the solution containing the enantiomeric mixture. More particularly, the % ee of the S-enantiomer 1a formed by treating a racemic modification 1a and 1b with varying amounts of dibenzoyl-D-tartaric acid as resolving agent and acetonitrile as solvent was determined, and the results are summarized in the following Table.

TABLE 1

Percent Enantiomeric Excess (% ee) as a function of solvent volume and amount of resolving agent

| Solvent Volume (ml) | Chiral Acid (eg) | % ee | Enantiomer Configuration |
|---|---|---|---|
| 50 | 1.0 | 47.4 | 1b (R-form) |
| 90 | 0.7 | 63.1 | 1a (S-form) |
| 95 | 0.6 | 88.7 | 1a (S-form) |
| 65 | 0.6 | 66.4 | 1a (S-form) |
| 30 | 0.5 | 88.2 | 1a (S-form) |

The results in Table 1 show that formation of the S-enantiomer 1a is favored by utilizing less than a stoichiometric amount of the chiral acid relative to the enantiomers in the mixture. When a stoichiometric amount of the chiral acid is employed or when the chiral acid is employed in stoichiometric excess, formation of the R-enantiomer 1b is favored.

Table 1 shows that the % ee can be increased by reducing the amount of the resolving agent even though there may be a slight increase in the solvent volume. (Compare the amount of acid and solvent for % ee=88.7 with % ee=63.1.)

The results in Table 1 further show that the percent enantiomeric excess can be affected by solvent volume. For example, when the amount of acid was held constant at 0.6 equivalents and the solvent volume reduced from 95 ml to 65 ml, % ee dropped to 66.4% from 88.7%.

The last entry in Table 1 shows that a high percent enantiomeric excess (% ee) can be achieved even though the solvent volume and the amount of resolving agent are relatively low.

The yield of the tartaric acid salt in the enrichment process of the invention can be optimized with a minimum of experimentation. The yield of the tartaric acid salt will generally be at least about 39%, preferably at least about 72%. Yields of at least about 77% can be readily obtained by optimizing the solvent volume and the amount of the resolving agent.

The concentrations of the enantiomers in a mixture can be determined by (1) treating the primary amine with (−)-menthyl chloroformate, followed by HPLC analysis of the corresponding diastereomeric carbamates; or (2) by treating the amine with (+)-camphorsulfonyl chloride, followed by HPLC analysis of the corresponding sulfonamide. The relative composition of a mixture of enantiomers is given by the areas under the peaks corresponding to the diastereomers in HPLC chromatograms.

The absolute configuration of the enantiomer is assigned by converting the amines to known compounds whose absolute configurations have been established. For example, the absolute configuration of the carbon atom at the 10-position of the primary amine can be determined by converting the tartaric acid salts of amines 1a or 1b into the corresponding optically pure primary amine 1a or 1b by neutralization with dilute NaOH. The resulting optically pure primary amine can be reductively cyclized in high yield by refluxing the amine in n-butanol in the presence of excess sodium metal. The product can then be derivatized with (s)-(−)-α-methylbenzyl isocyanate. The optical purity of the resulting product can be confirmed by HPLC analysis according to the method of Schonenberger and Brossi, Helv. Chim. Acta., 69:1486 (1986).

This invention will be more fully understood by reference to the following examples in which all parts, proportions, ratios, and percentages are by weight unless otherwise indicated.

A. Preparation of Enantiomeric Mixture

Example 1

Preparation of (±)-cyanomethyl-5-methoxy-1,3-dimethyloxindole

To a mixture containing 50 g of 5-methoxy-1,3-dimethyloxindole, 10.57 g of Aliquat 366 in 375 ml of toluene and 100 ml of 50% NaOH was added dropwise under nitrogen, a solution containing 21.73 g of chloroacetonitrile in 125 ml of toluene over 30 min. A slightly exothermic reaction ensued (50° C.). The reaction mixture was stirred for another 10 minutes, and then cooled to 10° C. To this cooled reaction mixture was added 400 ml of ice-cold water. The reaction mixture was transferred to a separatory funnel. The layers were separated and the organic layer was extracted with 3N HCl (2×250 ml) and water (1×250 ml). The toluene extract was concentrated under reduced pressure and the resultant dark oil was filtered through silica gel (500 g) eluting with 3% methanol-methylene chloride mixture. The eluate (2 L) was concentrated to give the target compound as an oil (54.61 g; 91% yield) which slowly crystallized upon seeding. This material was sufficiently pure and was reduced to (±)-1,3-dimethyl-5-methoxy-oxindolylethylamine without further purification. A small sample of (±)-cyanomethyl-5-methoxy-1,3-dimethyloxindole was recrystallized from isopropyl ether, m.p.=75.5°–76° C. (lit: 75°–76° C.).

Example 2

Preparation of (±)-1,3-Dimethyl-5-methoxyoxindolylethylamine

A mixture containing 18.5 g of (±)-cyanomethyl-5-methoxy-1,3-dimethyloxindole from Example 1, 27 ml of concentrated HCl, and 1.85 g of $PtO_2$ in 185 ml of methanol was hydrogenated using a Parr shaker under 45 psi of hydrogen. The progress of the reaction can be monitored by means of HPLC. After 1.5 hr, reaction was complete. The reaction mixture was filtered, and the filtrate was concentrated under reduced pressure. The residue was dissolved in ice-cold water (200 ml), treated with 50% NaOH (15 ml), and then extracted with methylene chloride (2×100 ml; 1×50 ml). The combined extracts were dried ($Na_2SO_4$) and concentrated under reduced pressure to give (±)-1,3-dimethyl-5-methoxy-oxindolylethylamine as a thick oil (17.81 g; 95%).

B. The Enrichment Process

Chemical Resolution of (+)-1,3-Dimethyl-5-methoxyoxindolylethylamine

Example 3

To a stirred solution containing 8.74 g of (±)-1,3-dimethyl-5-methoxy-oxindolylethylamine from Example 2 in 45 ml of acetonitrile at room temperature was added under nitrogen, a solution containing 8.42 g (0.6 eq.) of acid dibenzoyl D-tartaric acid in 40 ml of acetonitrile. After stirring the reaction mixture overnight, the precipitate that formed was filtered to give 5.50 g of a white solid which can be shown to be a mixture of 5.19 g of diastereomeric salt:

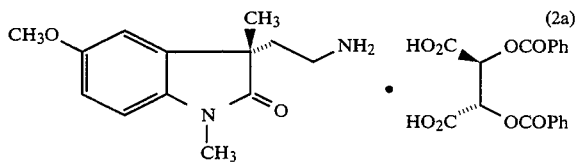

and 0.31 g of diastereomeric salt:

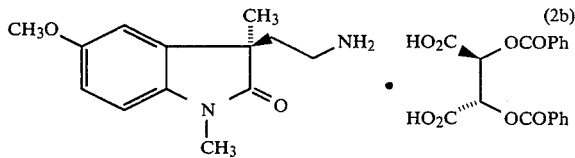

The composition of the above mixture was determined as follows: A sample of 0.61 g of the solid mixture was dissolved in 50 ml of 1% NaOH mixture, and extracted with 10 ml of methylene chloride. The organic extract was dried (Na₂SO₄) and treated with 0.15 ml of triethylamine and 0.21 ml of (−)-menthyl chloroformate at 0° C. for 15 min., and then at room temperature for 1 hr. The reaction mixture was analyzed by HPLC on a Whatmann Partisil PXS 10/25 column eluting with 10% acetonitrile/methylene chloride (2 ml/min; 254 nmdetection).

Example 4

To a stirred solution containing 8.10 g of amine (±)-1,3-dimethyl-5-methoxy-oxindolylethylamine in 65 ml of acetonitrile under nitrogen was added 7.81 g (0.6 eq) of acid dibenzoyl-D-tartaric acid in 1 portion. The mixture was stirred for 1.5 hr., and the precipitate that formed was filtered to give 9.70 g of a white solid (m.p.=130–136° C.), which can be shown to be a mixture containing 8.07 g of diastereomeric salt 2a and 1.63 g of diastereomeric salt 2b. The composition of the above solid mixture was determined as described in Example 3, except that the (−)-menthyl chloroformate derivatized amines 1a and 1b were analyzed by HPLC on a Cyclobond I column eluting with 50/50 water/methanol mixture (0.6 ml/min; 254 nm detection).

Example 5

To a stirred solution containing 7.20 g of amine, (±)1,3-dimethyl-5-methoxy-oxindolylethylamines, in 90 ml of acetonitrile under nitrogen was added 8.10 g (0.7 eq) of acid dibenzoyl-D-tartaric acid in 1 portion. The precipitate that formed was filtered to give 9.42 g of a white solid which can be shown to be a mixture containing 7.68 g of diastereomeric salt 2a and 1.74 g of diastereomeric salt 2b by methods described in Example 3.

Example 6

To a stirred solution containing 3.72 g of amine (±)-1,3-dimethyl-5-methoxy-oxindolylethylamines in 30 ml of acetonitrile under nitrogen was added 2.99 g (0.5 eq) of acid dibenzoyl-D-tartaric acid in 1 portion. There was obtained 2.05 g of a white solid which can be shown to be a mixture containing 1.93 g of diastereomeric salt 2a and 0.12 g of diastereomeric salt 2b by methods described in Example 3.

Example 7

To a stirred solution containing 3.92 g of amine (±)-1,3-dimethyl-5-methoxy-oxindolylethylamines in 20 ml of acetonitrile at room temperature was added under nitrogen a solution containing 6.30 g (1.0 eq) of acid dibenzoyl-D-tartaric acid in 30 ml of acetonitrile. The precipitate that formed was filtered to give 4.19 g of a white solid which can be shown to be a mixture containing 1.11 g of diastereomeric salt 2b and 3.08 g of diastereomeric salt 2a by methods described in Example 3. After several hours, a precipitate was deposited from the filtrate. This was filtered to give 4.33 g of a white solid which was shown to be a mixture containing 3.14 g of diastereomeric salt 2a and 1.19 g of diastereomeric salt 2b by methods described in Example 3.

C. The Recrystallization Process

Example 8

Recrystallization of 9.0 g of the solid mixture from Example 4 from 54 ml of 10% water/acetonitrile gave 6.0 g of white needles (m.p.=136–137.5° C.) which can be shown to contain greater than 98% of diastereomeric salt 2a by derivation using (−)-menthyl chloroformate followed by HPLC analysis as described in Example 4.

Example 9

A sample of 4.0 g of the 2a enriched mixture from Example 7 was further recrystallized from 75 ml of a 50/50 mixture of 2-butanone/acetonitrile to give 2.30 g of a white solid which was shown to contain greater than 95% of diastereomeric salt 2a.

Example 10

Recrystallization of a 10.38 g sample of (2a) enriched (>80% ee.) diastereomeric salt from 60 ml of a 10% water/acetonitrile gave 7.86 g of white needles (m.p.=136°–137° C.). This solid was shown to be essentially pure (>99%) compound 2a by derivation with (+)-camphorsulfonyl chloride followed by HPLC analysis of the sulfonamide on a Cyclobond I column eluting with a 50/50 -methanol/water mixture ( 0.6 ml/min; 254 nm detection ).

D. Isolating Enantiomer 1b

Example 11

The mother liquor from Example 3 was concentrated under reduced pressure, and the residue taken up in 100 ml of 2% NaOH solution. The aqueous mixture was extracted with methylene chloride. After concentration, the residue (6.63 g) was treated with dibenzoyl-L-tartaric acid (10.65 g) in acetonitrile. A white solid (11.82 g) was deposited. A sample of 10 g of this material was recrystallized from 225 ml of methyl ethyl ketone and 200 ml of acetonitrile giving 6.0 g of a solid which can be shown to contain at least 95% of enantiomer 1b after neutralization and derivation with (−)-menthyl chloroformate followed by HPLC analysis by methods described in Example 3.

In summary, this invention provides a simple method for chemically resolving the enantiomers of primary amines, such as 1,3-dimethyl-5 -methoxyoxindolylethylamine, in high yield using relatively inexpensive, commercially available reagents. The isomers can be obtained in high enantiomeric excess, and the isomers can be purified even further using well known recrystallization techniques. In addition, the process can be repeated on the mother liquor remaining after the first crop is recovered from a solution of enantiomers in order to increase product yield or to recover the other enantiomer from the mother liquor. The resulting purified compounds are useful for the preparation of physostigmine and pharmaceutically active physostigmine-like compounds. See e.g. U.S. Pat. No. 4,791,107.

What is claimed is:

1. A process for treating a mixture of enantiomers to precipitate one of the enantiomers from the mixture, wherein the process comprises:

(A) providing a solution consisting essentially of a mixture of enantiomers of the following formulas:

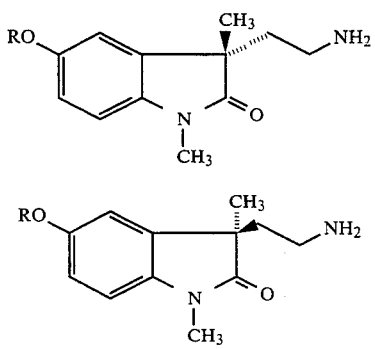

where R is a straight chain or branched alkyl group having 1-3 carbon atoms or benzyl;

(B) contacting the mixture with a chiral acid in an amount sufficient to preferentially precipitate a salt of the chiral acid and one of the enantiomers; and (C) recovering the resulting precipitate;

wherein the chiral acid is selected from the group consisting of dibenzoyl-D-tartaric acid, dibenzoyl-L-tartaric acid, ditoluoyl-D-tartaric acid, and ditoluoyl-L-tartaric acid.

2. Process as claimed in claim 1, wherein the mixture of enantiomers is a racemic mixture.

3. Process as claimed in claim 2, wherein the chiral acid is dibenzoyl-D-tartaric acid or ditoluoyl-D-tartaric acid.

4. Process as claimed in claim 3, wherein the precipitate comprises a salt of the formula:

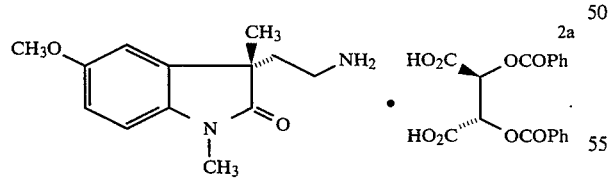

5. Process as claimed in claim 2, wherein the precipitate is recovered from a mother liquor containing the enantiomers, and the mother liquor is contacted with one of said chiral acids to preferentially form a second precipitate comprising a salt of the acid and one of the enantiomers.

6. Process as claimed in claim 5, wherein the mother liquor is contacted with dibenzoyl-D-tartaric acid or ditoluoyl-D-tartaric acid.

7. Process as claimed in claim 3, wherein the precipitate comprises a first salt of the formula:

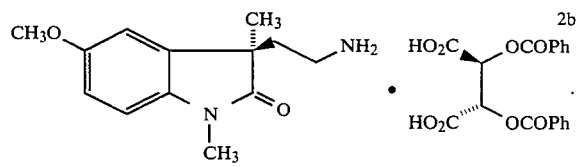

8. Process as claimed in claim 7, wherein the first salt is recovered from a mother liquor containing the enantiomers, and the mother liquor is contacted with one of said chiral acids to preferentially form a second salt of one of the enantiomers.

9. Process as claimed in claim 8, wherein the mother liquor is contacted with dibenzoyl-D-tartaric acid or ditoluoyl-D-tartaric acid and the second salt has the formula:

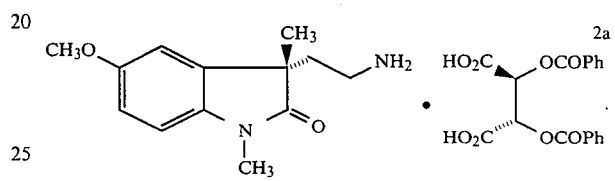

10. Process as claimed in claim 2, wherein the chiral acid is dibenzoyl-L-tartaric acid or ditoluoyl-L-tartaric acid.

11. A process for treating a mixture of enantiomers to remove one of the enantiomers from the mixture, wherein the process comprises:

(A) providing a solution consisting essentially of a mixture of enantiomers of the following formulas:

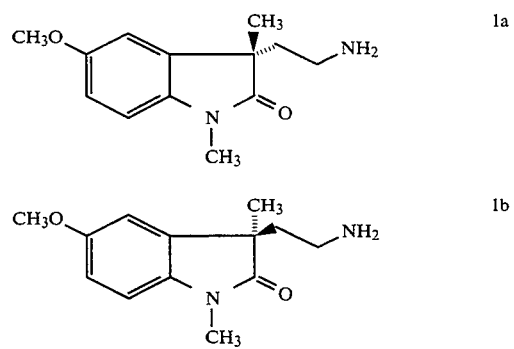

in an organic solvent therefor, wherein the ratio of solvent to enantiomers is about 5:1 to about 15:1 expressed as volume of solvent to total weight of enantiomers;

(B) contacting the mixture with a chiral acid in an amount less than a stoichiometric amount to preferentially precipitate a salt of the formula:

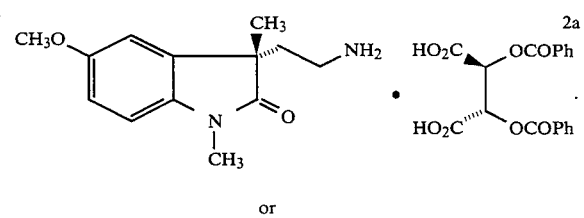

or

-continued

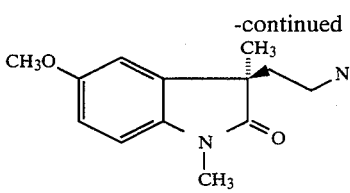 · 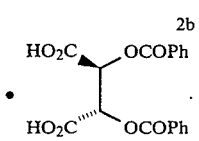 2b (C) and recovering the resulting precipitate;
wherein the chiral acid is selected from the group consisting of dibenzoyl-D-tartaric acid and ditoluoyl-D-tartaric acid.

12. Process as claimed in claim 11, wherein the mixture of enantiomers is a racemic mixture.

13. Process as claimed in claim 12, wherein the ratio of the volume of solvent to the total weight of enantiomers is about 8: 1 to about 12: 1.

14. Process as claimed in claim 12, wherein the ratio of the volume of solvent to the total weight of enantiomers is about 10:1.

15. Process as claimed in claim 12, wherein the solvent is acetonitrile.

16. Process as claimed in claim 12, wherein the chiral acid is employed in an amount of about 0.5 to about 1 equivalents of acid per equivalent of enantiomers.

17. Process as claimed in claim 16, wherein the chiral acid is employed in an amount of about 0.6 to about 0.7 equivalents of acid per equivalent enantiomers.

18. Process as claimed in claim 17, wherein the chiral acid is employed in an amount of about 0.85 equivalent per equivalent of the enantiomers.

19. Process as claimed in claim 12, wherein the organic solvent is selected from the group consisting of diethyl ether, methylene chloride, and chloroform, tetrahydrofuran, and dioxane.

20. A process for treating a mixture of enantiomers to remove one of the enantiomers from the mixture, wherein the process comprises:
(A) providing a solution consisting essentially of a mixture of enantiomers of the following formulas:

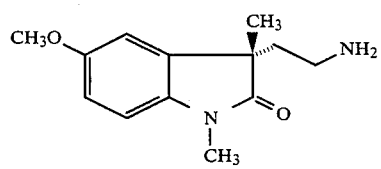 1a and

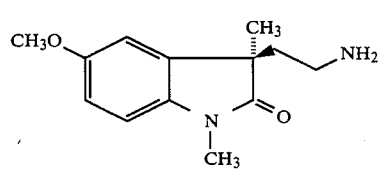 1b in an organic solvent therefor, wherein the ratio of solvent to enantiomers is about 8:1 to about 12:1 expressed as volume of solvent to total weight of enantiomers;
(B) contacting the mixture with dibenzoyl-D tartaric acid in an amount less than a stoichiometric amount to preferentially precipitate a salt of the formula:

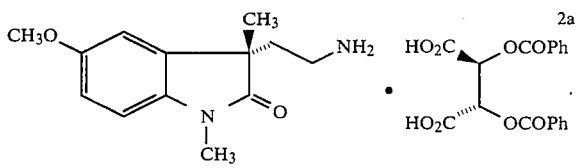 2a (C) recovering the resulting precipitate.

21. A process for treating a mixture of enantiomers to precipitate one of the enantiomers from the mixture, wherein the process comprises:
(A) providing a solution consisting essentially of a mixture of enantiomers of the following formulas:

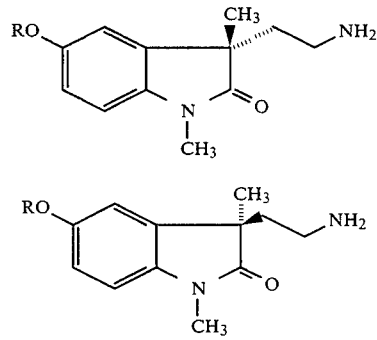

where R is a straight chain or branched alkyl group having 1-3 carbon atoms or benzyl;
(B) contacting the mixture with a chiral acid in an amount sufficient to preferentially precipitate a salt of the chiral acid and one of the enantiomers; and
(C) basifying the resulting tartaric acid salt to form the corresponding free base;
wherein the chiral acid is selected from the group consisting of dibenzoyl-D-tartaric acid, dibenzoyl-L-tartaric acid, ditoluoyl-D-tartaric acid, and ditoluoyl-L-tartaric acid.

22. Process as claimed in claim 21, wherein the tartaric acid salt is dissolved in water and the resulting solution is neutralized with an aqueous inorganic base.

23. Process as claimed in claim 22, which further comprises extracting amine from the aqueous solution with an organic solvent and isolating the amine by evaporation of the solvent.

24. Process as claimed in claim 23, wherein the solvent is selected from the group consisting of methylene chloride, ethyl acetate, diethyl ether, and toluene.

25. Process as claimed in claim 24, wherein the inorganic base is selected from the group consisting of sodium hydroxide, potassium hydroxide, sodium carbonate, and potassium carbonate.

* * * * *

UNITED STATES PATENT AND TRADEMARK OFFICE
CERTIFICATE OF CORRECTION

PATENT NO. : 5,387,695
DATED : February 7, 1995
INVENTOR(S) : Thomas B.K. Lee et al.

It is certified that error appears in the above-indentified patent and that said Letters Patent is hereby corrected as shown below:

IN THE TITLE, line 4, "(+)" should be --(±)--.

Signed and Sealed this

Thirteenth Day of June, 1995

Attest:

BRUCE LEHMAN

Attesting Officer     Commissioner of Patents and Trademarks